United States Patent [19]

Spiegel et al.

[11] Patent Number: 5,045,308

[45] Date of Patent: Sep. 3, 1991

[54] COSMETIC COMPOSITION

[75] Inventors: Udo Spiegel, Bielefeld, Fed. Rep. of Germany; Desmond B. Hagan, Little Sutton, England

[73] Assignee: Chesebrough-Pond's U.S.A. Co., Greenwich, Conn.

[21] Appl. No.: 367,070

[22] Filed: Jun. 16, 1989

[30] Foreign Application Priority Data

Jun. 16, 1988 [GB] United Kingdom ............... 8814295

[51] Int. Cl.$^5$ ..................... A61K 7/00; A61K 7/04
[52] U.S. Cl. ........................... 424/61; 424/59; 424/70; 424/401; 514/784; 514/844
[58] Field of Search ............... 514/844, 784; 424/59, 424/70, 401, 61

[56] References Cited

U.S. PATENT DOCUMENTS

| | | | |
|---|---|---|---|
| 4,038,418 | 7/1977 | Moller et al. | 514/784 |
| 4,105,782 | 8/1978 | Yu et al. | 424/DIG. 4 |
| 4,105,783 | 8/1978 | Yu et al. | 424/283 |
| 4,179,392 | 12/1979 | Heiba et al. | 252/DIG. 6 |
| 4,197,316 | 4/1980 | Yu et al. | 424/317 |
| 4,234,599 | 11/1980 | Yu et al. | 424/279 |
| 4,315,825 | 2/1982 | Schweizer et al. | 252/41 |
| 4,363,815 | 12/1982 | Yu et al. | 424/274 |
| 4,486,328 | 12/1984 | Knott et al. | 252/117 |
| 4,818,440 | 4/1989 | Schafer et al. | 514/844 |

FOREIGN PATENT DOCUMENTS

| | | |
|---|---|---|
| 0007785 | 2/1980 | European Pat. Off. |
| 1232569 | 11/1972 | United Kingdom . |
| 1471679 | 4/1977 | United Kingdom . |

*Primary Examiner*—Thurman K. Page
*Assistant Examiner*—James M. Spear
*Attorney, Agent, or Firm*—Milton L. Honig

[57] ABSTRACT

An acid-soap complex comprises:
(i) at least two 2-hydroxyalkanoic acid moieties of carbon chain length $C_m$ and $C_n$ respectively, where m and n have the same or different values, and each is an integer of from 6 to 28; and
(ii) a cation;
the complex having an elemental analysis of:

$$(C_mH_{2m-1}O_3)(C_nH_{2n-1}O_3) M$$

where M is the cation.

A process for preparing the complex and its use in compositions suitable for topical application to human skin, hair and nails is also claimed.

4 Claims, No Drawings

COSMETIC COMPOSITION

FIELD OF INVENTION

The invention relates to acid-soap complexes of 2-hydroxyalkanoic acids with a cation, to a process for preparing such complexes, and to their use in compositions for topical application to skin, hair and nails.

BACKGROUND

Certain 2-hydroxyalkanoic acids are known for their skin benefits when included in compositions for topical application to the skin. Such benefits include both increased elasticity of the skin, particularly the stratum corneum, and improved appearance. However, when included in skin cosmetic formulations, 2-hydroxyalkanoic acids are generally efficacious only at low pH. At high pH values, the efficacy of these acids appears to be reduced. Low pH formulations are less acceptable to consumers than are formulations of closer to neutral pH, in view of the possibility that they may cause irritation to sensitive skin and to the eyes.

PRIOR ART

EP-A 0 007 785 (Unilever) discloses skin treatment compositions incorporating α-hydroxycaproic acid or α-hydroxycaprylic acid or mixtures thereof, the compositions having a pH value of less than 7, usually from pH values of from 2 to 4. The pH value of the composition in Example 2 is likely to be below 3.85, the $pK_a$ of α-hydroxycaprylic acid.

It is proposed in U.S. Pat. No. 4,105,782 (Yu & Van Scott) to use amides or ammonium salts of α-hydroxyacids in the treatment of acne or dandruff and, in the Yu & Van Scott patents, U.S. Pat No. 4,105,783 and U.S. Pat. No. 4,197,316, to use such compounds in the treatment of dry skin. U.S. Pat. No. 4,234,599 (Yu & Van Scott) discloses the use of α-hydroxyacids, and their esters or amine salts in the treatment of keratoses. In all of these U.S. patents, the maximum carbon chain length is 6. In none of them is there any reference to the incorporation of alkali metal ions that could form complexes with the acids. In U.S. Pat. No. 4,363,815 (Yu & Van Scott) it is proposed to use α-hydroxyacids or β-hydroxyacids or ketoacids or their derivatives, including inorganic salts, in a composition for treating skin conditions. Suggested cations are calcium and magnesium, neither of which forms an acid-soap complex with α-hydroxyacids.

According to GB 1 471 679 (Avon), it is known to use alkali metal salts of $C_2$–$C_5$ α-hydroxycarboxylic acids in moisturizing compositions, but there is no mention of acid-soap complexes of the corresponding acids with alkali metal ions.

In DE 2 110 993 (Henkel), there are disclosed alkali metal salts of $C_4$–$C_{10}$ α-hydroxycarboxylic acids, and the sodium salt of α-hydroxycaprylic acid is mentioned. These salts are incorporated in amounts from 3–30% into washing and cleaning compositions and are said to confer improved storage stability. However, there is no mentioned of the pH values at which an acid-soap complex would form.

GB 1 232 569 (Medisan) discloses a skin-treating composition incorporating lactic acid and sodium chloride. There is a suggestion that a complex forms between urea and lactic acid, but no indication that the pH value is suitable for the formation of a sodium-lactic acid complex or salt. Indeed, it is highly improbable that an acid-soap complex would be formed.

DE 2 924 452 (Stange B) discloses a meat additive containing $C_1$ to $C_6$ hydroxycarboxylic acids and their sodium partial or full salts. However, there is no suggestion that an acid-soap complex will form.

It has now surprisingly been found that when 2-hydroxyalkanoic acids are complexed with alkali metal ions under certain very special conditions, the resulting acid-soap complexes are capable of forming at acid pH, compositions that are storage stable even at pH values around 7.

It has also been discovered that topical application of the complex to skin results in an increase in skin flexibility, with the result that the pliability of the skin is improved. This improvement is greater than that which can be obtained when using the corresponding salt of the free acid. The complex can be used in an insoluble form and a surprising benefit can be seen.

A further advantage resides in employing the composition for skin treatment at a pH value nearer the natural pH of human skin, which is higher than that associated with the use of corresponding free acid-containing composition. Compositions containing the acid-soap complex accordingly produce few of the common consumer-related problems associated with low pH, such as eye irritation.

The invention is accordingly concerned with a new acid-soap complex and compositions containing the complex which are suited to topical application to human skin, hair and nails.

DEFINITION OF THE INVENTION

Compound Per Se

The invention provides an acid soap complex comprising:
(i) at least two 2-hydroxyalkanoic acid moieties of carbon chain length $C_m$ and $C_n$ respectively, where m and n have the same or different values, and each is an integer of from 6 to 28; and
(ii) a cation;
the complex having an elemental analysis of:

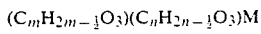

where M is the cation.

The invention also provides a process for preparing the complex and skin, hair and nail treatment compositions incorporating the complex.

DISCLOSURE OF THE INVENTION

The 2-hydroxyalkanoic acid-soap complex

The 2-hydroxyalkanoic acid-soap complex has an elemental analysis of:

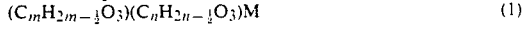
(1)

where m and n have the same or different values, and each is an integer of from 6 to 28, and M is a cation.

When the value of m or n is less than 6, the corresponding acid-soap complex is not formed to any significant extent, and when the value of m or n is greater than 28, the usefulness of the complex, as in the topical treatment of skin, which will be described later, is negligible.

The cation M is a monovalent ion such as potassium, sodium or ammonium. In certain circumstances, the cation M can alternatively be lithium, rubidium or caesium. Monovalent cations, such as these derived from substituted amines, for example alkanolamines, do not appear to form an acid-soap complex.

The 2-hydroxyalkanoic acid-soap complex is characterized as shown in the Table 1 below which gives typical values of selected acid-soap complexes, together with, by way of comparison, the free acid and corresponding simple salt.

TABLE 1

| COMPOUND | $^{13}$C RESONANCE (ppm) | | | IR ABSORPTION $\gamma(C=O)$ (cm$^{-1}$) |
|---|---|---|---|---|
| | C-1 | C-2 | C-$\omega$ | |
| C$_8$ acid | 177.5 | 70.2 | 13.6 | 1710 |
| Sodium salt of C$_8$ acid | 183.5 | 72.9 | 14.8 | 1580 |
| Sodium acid-soap complex of C$_8$ acid | 180.2 | 75.0 | 15.7 | 1745 |
| Potassium acid-soap of C$_8$ acid | 180.6 | 72.8 | 14.5 | 1730 |
| Ammonium acid-soap complex of C$_8$ acid | 180.1 | 72.7 | 15.1 | 1725 |
| Sodium acid-soap complex of C$_6$ acid | 180.2 | 74.7 | 15.6 | 1745 |
| Sodium acid-soap complex of C$_{10}$ acid | 180.2 | 74.8 | 15.3 | 1746 |
| Sodium acid-soap complex of C$_{12}$ acid | 180.2 | 74.7 | 15.3 | 1745 | where C-1, C-2 and C-$\omega$ are defined as follows:

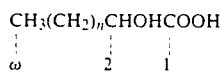

$$CH_3(CH_2)_n CHOHCOOH$$
$$\quad\quad\omega \quad\quad\quad 2 \quad 1$$

C$_6$ acid = 2-hydroxyhexanoic acid
C$_8$ acid = 2-hydroxyoctanoic acid
C$_{10}$ acid = 2-hydroxydecanoic acid
C$_{12}$ acid = 2-hydroxydodecanoic acid The $_{13}$C resonance of C-1 and the IR absorption of the carbonyl (C=O) bond are the most important from the point of view of analytical characterization of these compounds.

By Electron Spectroscopy for Chemical Analysis (ESCA), the sodium acid-soap complex of 2-hydroxy octanoic acid was found to have a carbon:oxygen:-sodium ratio of m+n:6:1. This is in agreement with the elemental analysis from which was derived the formula:

$$(C_mH_{2m-1}O_3)(C_nH_{2n-1}O_3)M \quad\quad (1)$$

The analytical data presented here confirm that there are physical differences between the structures of the free acid, the sodium salt and the sodium acid-soap complex.

PROCESS FOR PREPARING THE ACID-SOAP COMPLEX

The process according to the invention comprises contacting an aqueous solution of one or two 2-hydroxyalkanoic acids each having from 6 to 28 carbon atoms, with a cation at a pH value of 3.5 or more, and less than 7, to form a precipitate, and separating said precipitate to yield an acid-soap complex having an elemental analysis of:

$$(C_mH_{2m-1}O_3)(C_nH_{2n-1}O_3)M.$$

Preferably the cation is sodium, potassium or ammonium.

The preferred process comprises the steps of:

(a) dissolving the 2-hydroxyalkanoic acid(s) in water;
(b) adding to the solution so formed a cation-containing aqueous alkali to adjust the pH to 4, to form a precipitate; and
(c) filtering off the precipitate, washing with water and drying to obtain the complex as a fine white powder.

Optionally, step (b) may be followed by the addition of cations in aqueous solution and readjusting to pH 4 with aqueous alkali.

DEFINITION OF THE INVENTION

Composition

The invention also provides a composition for topical application to human skin which comprises the acid-soap complex as herein defined, together with a cosmetically acceptable vehicle and optionally conventional cosmetic adjuncts.

The Acid-Soap Complex

The acid-soap complex present in the composition according to the invention has the structure (1) as herein defined.

The preferred acid-soap complex is one in which m and n in structure (1) have the same value. Ideally this value is 8, but complexes where both m and n have a value of from 6 to 12 are also surprisingly effective in their skin benefit properties.

The preferred cation M in structure (1) in terms of skin benefit, is sodium, potassium or ammonium, the preferred acid soap complex having the empirical formula $C_{16}H_{31}O_6M$.

The acid-soap complex is present in the composition according to the invention in an amount of from 0.1 to 90%, preferably from 0.5 to 10% and ideally from 1 to 5% by weight of the composition.

The Cosmetically Acceptable Vehicle

The selection of a suitable vehicle will depend on the required product form of the composition. Typically, the vehicle will be chosen from diluents, dispersants or carriers for the acid-soap complex, so as to ensure an even distribution of the complex when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the composition, and can, in the absence of other cosmetic adjuncts, form the balance of the composition.

Cosmetic Adjuncts

Examples of conventional adjuncts which may optionally be employed include volatile silicones; silicone polymers; preservatives, such as para-hydroxy benzoate esters; humectants, such as butane-1,3-diol, glycerol, sorbitol, polyethylene glycol; stabilizers, such as sodium chloride or ammonium chloride; buffer system, such as lactic acid together with a base such as sodium hydroxide; oils and axes, such as avocado oil, Evening Primrose oil, sunflower oil, beeswax, ozokerite wax, paraffin wax, lanolin, lanolin alcohol; emollients; thickeners; activity enhancers; colourants; perfumes; emulsifiers; sunscreens; bactericides and water.

Cosmetic adjuncts can form up to 50% by weight of the composition and can conveniently form the balance of the composition.

pH

The composition according to the invention should preferably have a pH value of from 3.5 to <7.

It is apparent that difficulty may be experienced in obtaining the acid-soap complex, or retaining it as such, in the composition if the pH value is outside this range. At pH values below 3.5, there is tendency for the free acid to exist rather than the acid soap complex, and at pH values of 7 and above, there is a tendency for the corresponding salt to form rather than the complex.

Process for Preparing the Composition

The invention also provides a process for the preparation of a composition for topical application to human skin which comprises the step of incorporating the acid-soap complex, as herein defined, in a preformed state into the composition, together with a cosmetically acceptable vehicle.

The invention also provides a process for the preparation of a composition for topical application to human skin which comprises the steps of incorporating into the composition:

(a) one or two 2-hydroxy alkanoic acids having from 6 to 28 carbon atoms to provide a solution of said acid(s):

(b) a monovalent cation to react with said acid at a pH value of from 3.5 to <7 to form the corresponding acid-soap complex in situ in the composition; and (c) a cosmetically acceptable vehicle.

PRODUCT FORMS AND PACKAGING

The topical skin treatment composition of the invention can be formulated as a fluid, for example in a product such as a lotion, with or without an applicator such as a roll-ball applicator, or a propellant-driven aerosol device or a container fitted with a pump to dispense the composition, for example as a mousse or simply for storage in a non-deformable bottle or squeeze container. Alternatively, the composition of the invention may be solid or semi-solid, for example a cream or ointment, for use in conjunction with a suitable applicator, or simply for storage in a tube or lidded jar.

The invention accordingly also provides a closed container containing a cosmetically acceptable composition as herein defined.

EVIDENCE OF THE SUPERIORITY OF THE INVENTION

The following experiments compare the extensibility of the stratum corneum when treated either with the acid-soap complex of the invention or with the corresponding salt or free acid.

Measurements of extensibility were made as described in EP-A 0 007 785. For each sample of stratum corneum, an extensibility ratio was calculated as the ratio of the extensibility measurement for a treated sample to the measurement for an untreated control sample.

Experiment 1

An in vitro extensibility study was carried out on stratum corneum samples from guinea pig foot pads. Measurements of extensibility were made at a relative humidity of 61% and a temperature of 20° C. on batches of six samples of stratum corneum. Samples were treated with 1% by weight aqueous solution of the sodium, potassium or ammonium acid-soap complexes of 2-hydroxyoctanoic acid maintained at pH 4.0 with the corresponding base (hydroxide), and then compared with samples treated with 1% w/v aqueous solutions of sodium 2-hydroxyoctanoate at pH 7 and 10.3.

These experiments were repeated using the same materials as 2% w/v aqueous solutions.

The results are detailed in Table 2 below.

TABLE 2

| Active | pH | pH Adjustant | Extensibility Ratio |
|---|---|---|---|
| All results are at 1% concentration and deal with 2-hydroxy octanoic acid ($c_8$) | | | |
| Sodium salt | 7.00 | HCl | 1.07 ± 0.20 |
| Sodium salt | 10.30 | — | 0.97 ± 0.22 |
| Sodium acid-soap | 4.00 | NaOH | 1.86 ± 0.59 |
| Potassium acid-soap | 4.00 | KOH | 2.26 ± 0.46 |
| Ammonium acid-soap | 4.00 | NH$_4$OH | 1.57 ± 0.30 |
| All results are at 2% concentration and deal with 2-hydroxy octanoic acid ($C_8$) | | | |
| Sodium salt | 7.00 | HCl | 1.23 ± 0.16 |
| Sodium salt | 10.70 | — | 1.03 ± 0.13 |

TABLE 2-continued

| Active | pH | pH Adjustant | Extensibility Ratio |
| --- | --- | --- | --- |
| Sodium acid-soap | 4.00 | NaOH | 2.44 ± 0.84 |
| Potassium acid-soap | 4.00 | KOH | 4.98 ± 1.74 |
| Ammonium acid-soap | 4.00 | $NH_4OH$ | 4.33 ± 1.63 |

From these results it is apparent that the extensibility ratio of the stratum corneum was significantly greater at the 95% confidence level in the batches treated with acid-soap complex solutions than in the batches treated with the salt solution.

Experiment 2

This experiment compares the increase in extensibility conferred in vitro by solutions of the acid-soap complex and the free acid.

The tests were carried out on heat-separated guinea pig footpads which were immersed in the required solution at specified pH values. Extensibility ratios for each group of samples are shown in Table 3 below.

TABLE 3

| Active | pH | Extensibility Ratio | % Increase of Mean Ratio |
| --- | --- | --- | --- |
| 1% acid | 5.0 (b) | 0.82 ± 0.18 | |
| 1% complex | 5.0 (a) | 1.22 ± 0.20 | 48.8 |
| 2% acid | 5.0 (b) | 0.86 ± 0.22 | |
| 2% complex | 5.0 (a) | 1.53 ± 0.34 | 77.9 |
| 1% acid | 6.0 (b) | 0.94 ± 0.08 | |
| 1% complex | 6.0 (a) | 1.33 ± 0.21 | 41.5 |
| 2% acid | 6.0 (b) | 0.97 ± 0.10 | |
| 2% complex | 6.0 (a) | 1.27 ± 0.12 | 30.9 | acid = free acid (2-hydroxyoctanoic acid)
complex = sodium acid soap of 2-hydroxyoctanoic acid ($C_8$)
Note: the pH value was adjusted to the values shown above using either (a) sodium hydroxide or (b) triethanolamine.

The extensibility ratios for the 1% complex solution were significantly greater, at the 95% confidence level, than those of the 1% free acid solution at both pH 5 and 6.

The extensibility ratios for the 2% complex solution were significantly greater, at the 99% confidence level, than those of the 2% free acid solution at both pH 5 and 6.

These results clearly indicate that the complex has a greater effect on extensibility in vitro than does the free acid, in the natural pH range of skin.

Experiment 3

This experiment compares the extensibility increase conferred in vitro by solutions of the acid-soap and the free acid, in the presence of 13.5% w/w butane-1,3-diol, as an example of an activity enhancer.

The tests were carried out on heat-separated guinea pig footpads which were immersed in the required solution at specified pH values. Extensibility ratios for each group of samples are shown in Table 4 below.

TABLE 4

| Active | pH | Extensibility Ratio | % Increase of Mean Ratio |
| --- | --- | --- | --- |
| 1% acid | 5.0 (b) | 1.07 ± 0.30 | |
| 1% complex | 5.0 (a) | 2.25 ± 0.73 | 110.3 |
| 1% acid | 6.0 (b) | 1.68 ± 0.46 | |
| 1% complex | 6.0 (a) | 2.51 ± 0.54 | 49.4 | acid = free acid (2-hydroxyoctanoic acid)
complex = sodium acid soap of 2-hydroxyoctanoic acid ($C_8$)
Note: the pH value was adjusted to the value shown using either (a) sodium hydroxide, or (b) triethanolamine.

At both pH 5 and pH 6, the extensibility ratios for the complex in solution were significantly greater, at the 95% confidence level, than those of the free acid solution.

These results indicate that, for these solutions containing butane-1,3-diol, the acid-soap complex has a greater effect on extensibility in vitro than does the free acid.

EXAMPLES

The invention is further illustrated by the following examples.

Example 1

The example illustrates an oil-continuous (W/O) cream containing the sodium acid-soap complex of the $C_8$ hydroxy acid.

| Ingredients | % w/w |
| --- | --- |
| Silicones | 20.00 |
| Sodium chloride | 2.00 |
| Sodium acid-soap complex of 2-hydroxyoctanoic acid | 1.00 |
| Whitener | 0.15 |
| Preservatives | 0.36 |
| Lactic acid | 5.00 |
| Sodium hydroxide | 1.30 |
| Water | 70.19 |
| | 100.00 |

The skin cream, having a pH value of 4, is made by the process as herein described by adding gradually to a mixture of silicones, whitener and preservatives an aqueous mixture of the remaining ingredients and homogenizing.

Example 2

This example illustrates a w/o skin cream containing the ammonium acid-soap complex of the $C_{10}$ hydroxy acid, humectants and perfume.

| Ingredients | % w/w |
| --- | --- |
| Silicones | 20.00 |
| Whitener | 0.20 |
| Preservatives | 0.35 |
| Perfume | 0.15 |
| Ammonium acid-soap complex of 2-hydroxy decanoic acid | 1.00 |
| Ammonium hydroxide | 7.95 |
| Ammonium chloride | 2.00 |
| Humectant | 10.00 |
| Lactic acid | 5.00 |
| Water | 53.35 |
| | 100.00 |

The skin cream, having a pH value of 4.5, is made by the process as herein described by adding gradually to a mixture of silicones, whitener, perfume and preservatives an aqueous mixture of the remaining ingredients and homogenizing.

Example 3

This example illustrates a w/o skin cream containing sunscreens and the potassium acid-soap complex of the $C_{12}$ hydroxy acid, prepared in situ during the manufacture of the cream.

| Ingredients | % w/w |
|---|---|
| Silicones | 24.00 |
| Whitener | 0.15 |
| Preservatives | 0.05 |
| 2-Hydroxy dodecanoic acid | 1.00 |
| Potassium hydroxide | 4.00 |
| Potassium chloride | 2.00 |
| Humectants | 5.00 |
| Evening Primrose Oil | 3.00 |
| Sunscreens | 4.00 |
| Bactericides | 0.30 |
| Lactic acid | 5.00 |
| Water | 51.50 |
| | 100.00 |

The skin cream, having a pH value of 5, is made by the process as herein described by adding gradually to a mixture of silicones, whitener and preservatives an aqueous mixture of the remaining ingredients and homogenizing.

Example 4

This example illustrates a water-continuous (o/w) cream containing the ammonium acid-soap complex of the $C_8$ hydroxy acid and sunscreens.

| Ingredients | % w/w |
|---|---|
| Emulsifiers | 10.50 |
| Silicone oil | 7.60 |
| Thickener | 0.50 |
| Whitener | 0.20 |
| Preservatives | 0.10 |
| Ammonium acid-soap complex of 2-hydroxy octanoic acid | 1.00 |
| Ammonium hydroxide | 2.00 |
| Humectant | 10.00 |
| Evening Primrose Oil | 2.00 |
| Sunscreens | 3.00 |
| Bactericides | 0.30 |
| Lactic acid | 5.00 |
| Water | 57.80 |
| | 100.00 |

The skin cream, having a pH value of 4, is made by the process as herein described by adding to a heated mixture of emulsifiers, silicone oil, whitener and preservatives a mixture of the thickener, butanediol and 75% of the water and homogenizing. The remaining ingredients are added as an aqueous mixture with further homogenizing.

Example 5

This example illustrates a ater-continuous (o/w) lotion containing the ammonium acid-soap complex of the $C_{18}$ hydroxy acid.

| Ingredients | % w/w |
|---|---|
| Emulsifiers | 3.00 |
| Oils | 8.00 |
| Thickener | 0.35 |
| Whitener | 0.15 |
| Preservatives | 0.35 |
| Ammonium acid-soap complex of 2-hydroxy octadecanoic acid | 1.00 |
| Ammonium hydroxide | 3.95 |
| Butane-1,3-diol | 9.45 |
| Lactic acid | 3.75 |
| Water | 70.00 |
| | 100.00 |

Example 6

The example illustrates a gel suitable for treating hair containing the sodium acid-soap complex of the $C_{10}$ hydroxy acid.

| Ingredients | % w/w |
|---|---|
| Emulsifiers | 20.00 |
| Silicone oil | 20.00 |
| Sodium acid-soap complex of 2-hydroxy decanoic acid | 1.00 |
| Sodium hydroxide | 4.55 |
| Butane-1,3-diol | 11.00 |
| Lactic acid | 5.00 |
| Water | 38.45 |
| | 100.00 |

Example 7

This example illustrates an all-purpose face-mask containing the potassium acid-soap complex of the $C_{14}$ hydroxy acid.

| Ingredient | % |
|---|---|
| Kaolin | 35.00 |
| Bentonite | 5.00 |
| Cetyl alcohol | 2.00 |
| Potassium dodecyl sulphate | 1.00 |
| Glycerin | 10.00 |
| Nipagin M | 0.10 |
| Potassium acid-soap complex of 2-hydroxy tetradecanoic acid | 5.00 |
| Perfume | 5.00 |
| Water | 36.90 |
| | 100.00 |

The mask is made by the process, as herein described, by blending the mixture of the ingredients.

Example 8

This example illustrates a water-continuous (o/w) cream containing the potassium acid-soap complex of the $C_8$ hydroxy acid.

| Ingredient | % |
|---|---|
| Thickener | 0.50 |
| Preservatives | 0.36 |
| Whitener | 0.15 |
| Butane-1,3-diol | 13.50 |
| Emulsifiers | 10.35 |
| Silicone oil | 7.60 |
| Potassium acid-soap complex of $C_8$ acid | 1.00 |
| Potassium hydroxide | 3.00 |
| Lactic acid | 5.00 |
| Water | 58.54 |
| | 100.00 |

The skin cream, having a pH value of 4, is made by the process as herein described by adding to a heated mixture of emulsifiers, silicone oil, whitener and preservatives a mixture of the thickener, butanediol and 75% of the water and homogenizing. The remaining ingredients are added as an aqueous mixture with further homogenizing.

Example 9

This example illustrates a lotion suitable for treatment of nails containing the sodium acid-soap complex of the $C_{16}$ hydroxy acid.

| Ingredient | % |
|---|---|
| Sodium acid-soap complex of 2-hydroxy hexadecanoic acid | 6.00 |
| Sodium hydroxide | 1.50 |
| Ethanol | 10.00 |
| Propane-1,2-diol | 55.00 |
| Water | 27.50 |
|  | 100.00 |

This lotion, having a pH value of 4.4, is made by the process, as herein described, by homogenizing the mixture of the ingredients.

Example 10

This example illustrates a further w/o skin cream, in which the acid-soap complex is formed in situ in the composition.

| Ingredients | % w/w |
|---|---|
| Silicones | 24.00 |
| Sodium chloride | 2.00 |
| 2-hydroxyoctanoic acid | 1.00 |
| Lactic acid | 5.00 |
| Sodium hydroxide | 2.00 |
| Humectants | 5.00 |
| Whitener | 0.15 |
| Preservatives | 0.05 |
| Evening Primrose Oil | 3.00 |
| Sunscreens | 4.00 |
| Bactericides | 0.30 |
| Water | 53.50 |
|  | 100.00 |

The skin cream, having a pH value of 4, is made by the process as herein described by adding gradually to a mixture of silicones, whitener and preservatives a mixture of the remaining ingredients and homogenizing.

Example 11

This Example illustrates an oil-continuous (w/o) cream containing sunscreens.

| Ingredient | % |
|---|---|
| Silicones | 24.00 |
| Humectants | 5.00 |
| Whitener | 0.15 |
| Preservatives | 0.05 |
| Evening Primrose Oil | 3.00 |
| Sunscreens | 4.00 |
| Bactericides | 0.30 |
| Humectants | 5.00 |
| Ammonium acid-soap complex of 2-hydroxy hexanoic acid | 1.00 |
| Ammonium hydroxide | 2.00 |
| Ammonium chloride | 2.00 |
| Lactic acid | 5.00 |
| Water | 48.50 |
|  | 100.00 |

Example 12

This Example illustrates an oil-continuous (w/o) cream containing sunscreens.

| Ingredient | % |
|---|---|
| Silicones | 24.00 |
| Humectants | 5.00 |
| Whitener | 0.15 |
| Preservatives | 0.05 |
| Evening Primrose Oil | 3.00 |
| Sunscreens | 4.00 |
| Bactericides | 0.30 |
| Humectants | 5.00 |
| Ammonium acid-soap complex of 2-hydroxy hexanoic acid | 1.00 |
| Ammonium hydroxide | 2.00 |
| Ammonium chloride | 2.00 |
| Lactic acid | 5.00 |
| Water | 48.50 |
|  | 100.00 |

We claim:
1. An acid soap complex comprising:
   (i) at least two 2-hydroxyalkanoic acid moieties of carbon chain length $c_m$ and $c_n$ respectively, where m and n have the same or different values, and each is an integer of from 6 to 28; and
   (ii) a cation selected from the group consisting of lithium, sodium, potassium and ammonium cations; the complex having an elemental analysis of:

$$(C_mH_{2m-1}O_3)(C_nH_{2n-1}O_3)M$$

where M is the cation, and wherein said complex is formed in an aqueous solution at a pH value of from 3.5 to <7.

2. The acid-soap complex of claim 1, wherein m and n have the same value and each is an integer of from 6 to 12.

3. The acid-soap complex of claim 2, wherein m and n are each 8, the complex having the empirical formula:

$$C_{16}H_{31}O_6M.$$

4. A process for preparing an acid-soap complex which comprises the steps of:
   (i) contacting an aqueous solution of at least one 2-hydroxyalkanoic acid having from 6 to 28 carbon atoms, with a monovalent cation at a pH value of from 3.5 to <7, to form a precipitate; and
   (ii) separating said precipitate to yield an acid-soap complex having an elemental analysis of:

$$(C_mH_{2m-1}O_3)(C_nH_{2n-1}O_3)M$$

where M is the monovalent cation and is selected from the group consisting of lithium, sodium, potassium and ammonium cations, and m and n have the same or different values with each being an integer of from 6 to 28.

* * * * *

UNITED STATES PATENT AND TRADEMARK OFFICE
CERTIFICATE OF CORRECTION

PATENT NO. : 5,045,308

DATED : September 3, 1991

INVENTOR(S) : Udo Spiegel, Desmond B. Hagan

It is certified that error appears in the above-identified patent and that said Letters Patent is hereby corrected as shown below:

Title page, item [73], the Assignee should read:

--Chesebrough-Pond's USA Co., Division of Conopco, Inc.--.

In claim 1 located at column 12, line 38, the formula should read:

--$(C_m H_{2m-\frac{1}{2}} O_3)(C_n H_{2n-\frac{1}{2}} O_3)$ M--.

Signed and Sealed this

Tenth Day of August, 1993

Attest:

MICHAEL K. KIRK

Attesting Officer     Acting Commissioner of Patents and Trademarks